(12) United States Patent
McFarland, Jr.

(10) Patent No.: US 6,729,327 B2
(45) Date of Patent: May 4, 2004

(54) PORTABLE, HANDHELD, PNEUMATIC DRIVEN MEDICINAL NEBULIZER

(75) Inventor: Joseph L. McFarland, Jr., 1330 S. Yukon, Lakewood, CO (US) 80232

(73) Assignee: Joseph L. McFarland, Jr., Lakewood, CO (US)

( * ) Notice: Subject to any disclaimer, the term of this patent is extended or adjusted under 35 U.S.C. 154(b) by 0 days.

(21) Appl. No.: 10/322,314

(22) Filed: Dec. 17, 2002

(65) Prior Publication Data

US 2003/0121517 A1 Jul. 3, 2003

Related U.S. Application Data

(60) Provisional application No. 60/341,715, filed on Dec. 17, 2001.

(51) Int. Cl.$^7$ ............................................. A61M 15/00
(52) U.S. Cl. ............................... 128/203.12; 128/203.14
(58) Field of Search .................... 128/200.12, 200.21, 128/200.22, 203.12, 203.14, 203.15, 203.24, 203.25, 204.21, 204.22, 204.23, 204.25, 207.16, 200.14, 200.13, 200.19, 204.11, 205.25, 205.23, 205.21; 600/529; 222/129, 135, 137, 145.1, 145.5; 239/304, 311

(56) References Cited

U.S. PATENT DOCUMENTS

| 595,529 A | * | 12/1897 | Deyoung ..................... 188/115 |
| 2,428,425 A | | 10/1947 | Levitt ......................... 128/147 |
| 2,852,023 A | | 9/1958 | Hamilton et al. ........... 128/203 |
| 2,856,922 A | | 10/1958 | Kahan ......................... 128/203 |
| 2,970,594 A | | 2/1961 | Doak .......................... 128/203 |
| 3,045,671 A | * | 7/1962 | Updegraff .............. 128/205.21 |
| 3,119,561 A | * | 1/1964 | Wilson ....................... 239/309 |
| 3,326,231 A | * | 6/1967 | Hogg .......................... 137/318 |
| 3,645,286 A | | 2/1972 | Follett ......................... 137/68 |
| 3,932,153 A | * | 1/1976 | Byrns .......................... 55/511 |
| 4,077,422 A | | 3/1978 | Brinkley et al. ............... 137/68 |
| 4,454,877 A | * | 6/1984 | Miller et al. ............ 128/200.21 |
| 4,887,591 A | | 12/1989 | Okumura ................ 128/205.21 |
| 5,169,029 A | * | 12/1992 | Behar et al. .................... 222/1 |
| 5,299,565 A | * | 4/1994 | Brown .................. 128/200.21 |
| 5,318,015 A | * | 6/1994 | Mansson et al. ........ 128/200.22 |
| 5,653,223 A | * | 8/1997 | Pruitt ..................... 128/200.21 |
| 5,655,516 A | * | 8/1997 | Goodman et al. ...... 128/200.14 |
| 5,711,340 A | | 1/1998 | Gusky et al. ............. 137/68.19 |
| 5,813,397 A | * | 9/1998 | Goodman et al. ...... 128/200.14 |
| 6,024,699 A | * | 2/2000 | Surwit et al. ................ 600/300 |
| 6,102,856 A | * | 8/2000 | Groff et al. ................. 600/301 |
| 6,125,844 A | * | 10/2000 | Samiotes ................ 128/200.23 |
| 6,190,326 B1 | * | 2/2001 | McKinnon et al. .......... 600/529 |
| 6,225,901 B1 | * | 5/2001 | Kail, IV ...................... 340/539 |
| 6,550,472 B2 | * | 4/2003 | Litherland et al. ...... 128/200.18 |
| 6,626,171 B2 | * | 9/2003 | Sexton et al. .......... 128/200.23 |
| 2001/0039372 A1 | * | 11/2001 | Yasushi et al. .............. 600/300 |
| 2001/0044588 A1 | * | 11/2001 | Mault .......................... 600/549 |
| 2002/0005926 A1 | * | 1/2002 | Okada et al. ................ 349/129 |
| 2002/0019584 A1 | * | 2/2002 | Schulze et al. .............. 600/300 |
| 2002/0026103 A1 | * | 2/2002 | Norris et al. ................ 600/300 |
| 2002/0189612 A1 | * | 12/2002 | Rand ..................... 128/200.23 |

FOREIGN PATENT DOCUMENTS

DE 1153781 9/1963

* cited by examiner

*Primary Examiner*—Aaron J. Lewis
*Assistant Examiner*—Teena Mitchell
(74) *Attorney, Agent, or Firm*—Sheridan Ross P.C.

(57) ABSTRACT

A portable, handheld medicine delivery device capable producing atomized agents that are adapted to be inhaled through a nebulizer by a patient suffering from a respiratory condition. In addition, the present invention provides a means wherein the dose of the inhaled agent can be remotely monitored and, if required altered, by a physician or doctor. Finally, the present invention embodies an apparatus and method for reducing a high-pressure delivery gas into a lower pressure gas suitable for atomizing a medicinal agent and for inhalation.

17 Claims, 12 Drawing Sheets

PORTABLE, HANDHELD, PNEUMATIC DRIVEN MEDICINAL NEBULIZER

This application claims priority to, and incorporates by reference in its entirety, U.S. Provisional application No. 60/341,715 entitled PORTABLE, HANDHELD MEDICINAL NEBULIZER filed Dec. 17, 2001.

FIELD OF THE INVENTION

The present invention relates to an apparatus and method for administering an atomized liquid or powdered medication substance suitable for inhalation from a nebulizer, which utilizes a portable, handheld cartridge administrator of pressurized gas, such as oxygen. Moreover, the device has the capacity to integrate supplementary modules for servo-feedback diagnostic integration. This feature helps manage the desired therapeutic outcome of the inhaled agent. These outcomes include basic lung function (spirometry), blood oxygen levels (pulse oximetry), blood glucose levels (glucometer), basal metabolic rate (BMR for VO2Max) and other simple blood or exhaled gas diagnostics.

BACKGROUND OF THE INVENTION

The upper respiratory system is commonly defined as the nasopharynx (nose) oropharynx (mouth), laryngopharynx (larynx), trachea and sometimes includes the main stem bronchus and, right and left main stem bronchus. The lower respiratory tract continues through the terminal respiratory bronchioles alveolar ducts and ends with the alveolar sacs. Each progressive branch of the airways results in smaller diameters and shorter length until microscopic in size. Optimally, delivery of inhaled agents to the lower respiratory tract requires shattering a liquid or solid agent into a particle size range of between about 0.2 and 3.0 microns. Penetration of an inhaled agent is defined as the maximum depth that suspended particles can be carried into the respiratory system during a normal inspiratory effort. Deposition of the agent refers to the eventual instability of the particles resulting in a "fall out" on to a nearby surface. Four factors are directly related to the efficiency of deposition of optimal ranged particles: 1) kinetic activity; 2) pattern of respiratory activity; 3) gravity; and 4) inertial impaction. Kinetic Activity is defined as the erratic movement pattern of the medicinal agent irrespective of direction of flow, also known as the Brownian movement. Pattern of Respiratory Activity generally refers to the deposition and retention of inhaled particles which is directly related to inhaled volume and inversely related to ventilatory rate. Gravity refers to the influence of a suspended particle is in direct relation to the particle mass influenced by known and constant gravitational forces which follows Stokes law of Sedimentation. Finally, Inertial Impaction refers to the penetration and deposition of an inhaled agent which includes a strong influence of the theory of inertial impaction. Furthermore, this factor is based on the fact that water particles (and inhaled agents) have a greater mass than gas molecules. In addition, the force moving these particles in a straight line is greater than the force on gas molecules. When a change in direction, as in a splitting bronchiole, the probability of deposition caused by inertial impaction increases as the diameter of the conducting tube airway decreases in size. This is a significant factor in the smaller airways of the lower respiratory tract. Dose dilutions and frequency of inhaled agents has been established based on deposition of the inhaled agent(s) delivered in the optimal size range. Inhaled agents must be stable at a temperature range of 35 degrees Fahrenheit through 130 degrees Fahrenheit.

The unique nebulized features of this product is the ability to not only produce particle of optimal size for traditional inhalation to the lower respiratory tract, but also produces larger particle sizes for deposition into the upper respiratory tract. And, the unique baffling system and jet producing flows can be changed for purposeful alterations in speed of agent delivery (a factor of dilution effecting gravity, inertial impaction, and kinetic activity). Adding these features offers significant expanded utility to include non-traditional inhaled agents to effectively and efficiently be nebulized for targeted penetration and deposition that is not available within a single, mono-purpose nebulizer device. Monitoring the effectiveness of the inhaled agent and adjusting the controllable factors in a "servo-controlled defined protocol" adds an even greater and unique purpose and value to this system.

Many inhaled medications will have a greater safety and efficacy (dose, delivery and frequency) if a narrow window of precise medication can be delivered and cause/effect results can be directly measured, monitored and remotely adjusted. This concept is well understood with parallels seen in high blood pressure management and insulin therapy for diabetics but has not been possible for the delivery of inhaled agents. Furthermore, in some instances it is desirable to deposit agents into the upper respiratory tract, (including the nose and sinuses) transitional airways (trachea and main-stem bronchus) and lower airways for deep lung penetration. A device that included these features will open opportunities to treat traditional respiratory related diseases inflicted upon patients ranging from neonates through geriatrics. In addition, this new delivery and monitoring system provides a new foundation to inhale non-traditional drugs into the lungs such as insulin, antibiotics, pulmonary hypertension drugs, systemic hypertension drugs, hereditary enzyme deficiency replacement agents and neonatal lung-specific treatments. An additional market includes a modified, non-prescription device for naturopathic/homeopathic products. This is very promising as the general consumers in the U.S. and European markets are expanding with diet supplementation, improved vitamin absorption techniques and many new homeopathic treatment alternatives. Inhaling safe agents into the lungs is supported by clinical parameters of a highly vascularized, oxygen enriched and easily accessible delivery route for naturopathic and homeopathic supplements and treatment options.

One of two traditional markets of application includes the category of Chronic Obstructive Pulmonary Disease (COPD) which currently an estimated 16 million people in the United States are diagnosed as having. It is estimated that an additional 14 million or more are still undiagnosed, as they are in the beginning stages and have few or minimal symptoms and have not sought health care yet. COPD is an umbrella term used to describe lung disease associated with airflow obstruction. Most generally, emphysema, chronic bronchitis and chronic asthma either alone or in combinations fall into this category. There is continuing debate as to whether this term also includes Asthma (non chronic), however as a general rule, it is not included as, even though it does have obstructive components to it, it is in part reversible, and is more generally considered a restrictive lung disease.

The second traditional market is asthma. Asthma has been labeled as both a chronic lung and acute disease characterized by inflammation of the airways because of increased sensitivity to a variety of triggers, which can cause narrowing of the airways and breathing difficulty. Asthma affects 14.6 million Americans and increases by about 6% annually.

Of that number, 4.8 million are children under the age of 18. Asthma is the number one cause of school absences attributed to a chronic condition. More than 5,400 people in the United States die each year from asthma. Direct and indirect costs of asthma care exceed $6 billion each year. This includes loss of time from work and school, and medical costs. To recover the cost issues, improve the outcomes of therapy and reduce the risks for loss of life, better-nebulized drug delivery and response to therapy monitoring systems will be a required tool before medical scientists and disease management protocols experts deem the disease under better control.

In general, a standard commercial asthma nebulizer is an electromechanical device that requires pressurized air to atomize liquid medication into the form of a very fine aerosol mist for patient inhalation. The pressurized air is generated from an internal portable air compressor with a maximum pressure of between about 30 and 45 psig and is driven by an electrical AC motor that generates a noise level of about 53 dBA. The pressurized air exits the electrical motor and travels through a predetermined length of polyethylene tubing to a patient hand-held medicine chamber. The patient is required to manually measure and fill the medicine chamber (6 cc/ml) with various medications in predetermined amounts as prescribed by the doctor or physician. The medicine chamber is manufactured to specific geometries that determine a nebulization rate of between about 0.15 and 0.3 ml per minute and a flow rate of between about 6 to 8 liters per minute. The medication chamber is pressurized from between about 14 and 25 psig of room air, which contains approximately 21% oxygen and is forced through the medicine chamber. The result of this event is a very fine atomized mist of less than 1 micron particle size product in 80% of the population of medication that a patient inhales. The temperature of the gas inhaled by the patient is between about 80 to 90 degrees Fahrenheit, which is created from friction being generated inside the electrical compressor.

A standard commercial nebulizer has a footprint of about 7.0" wide×3.8" high×13.0" deep (18 cm×10 cm×33 cm) and weighs approximately 7 pounds to 12 pounds and requires an electrical outlet of 115VAC to operate. The treatment time with this type of device generally takes 10 minutes to 12 minutes to complete. Alternatively, ultrasonic nebulizers are an optional choice for some patients for portability and a have slightly more dispensing resolution in droplet particle size to the patient. However, to be mobile, the patient must hold these heavy units. Thus, the standard commercial asthma nebulizer is extremely large in size, burdensome and complicated to use and not generally practical to use as a portable, interim, self-sufficient device.

Thus, there is a long felt need in the field of chronic and acute respiratory care to provide a medicinal agent delivery system which is light, portable, easy to use and maintain, and is capable of servo-feedback diagnostic monitoring and real-time, physician-initiated, dosage regulation.

SUMMARY OF THE INVENTION

It is thus one aspect of the present invention to provide a technically advanced medicine nebulizing device and an associated environmental control unit for the device. The nebulizer device of the present invention is geometrically improved and considerably smaller, having the size of a miniature cellular phone, and being significantly lighter, weighing in one embodiment only about one pound, and providing more utility with virtually no mobility restrictions to the patient. The apparatus is portable enough to allow some critical care patients to leave home periodically or to travel and not require the use of an electrical outlet. The device also provides an advanced medicine delivery system attachment, which effectively allows for a hands-free operation. The medicine chamber is disposable and integrated into the patient's state of the art headset dispenser. The headset houses a prescribed medication module and in one embodiment a music adaptor such as media player, compact disc, etc. for patient relaxation during normal treatments. The media player mechanism will also support patient training, use, and maintenance of the device, as well as communication from a treating physician by way of the Internet or phone connection.

In another aspect of the present invention, a nebulizer device is provided which is a state-of-the-art electronic medicinal environmental control unit and headset dispenser system, which utilizes a global interface between the nebulizer device, a doctor or physician, and the patient end user. The medicinal dispensing system is adaptable and can be programmed for frequent, periodic, and continual prescription adjustments to medication dosages under the doctor's control using a cellular telephone, landline, the Internet, or by manual adjustments during office visits. Using a phone line or cellular connection will provide normal maintenance of prescription requirements, as well as provide emergency communication between the doctor, patient, and if necessary, an emergency 911 interface. In one embodiment of the present invention the patient's condition is remotely monitored when the system is in use. More specifically, the patient's reaction to the agent and gas flow are remotely accessed by a doctor who then compares the results of the treatment with a predetermined set of criteria or protocol. The doctor then can remotely adjust the dosage, gas flow, or both as required in order to more effectively treat the patient. Alternatively, a computer program may be used to initiate or monitor the treatment with software preprogrammed by the doctor. This automated monitoring and dosage regulation may also be accomplished with means incorporated into the system itself, wherein the protocol is initiated or adjusted during routine doctor's office visits. The information related to patent reactions, patient condition, and dosage history, for example may be stored to facilitate the doctor's review of patient progress.

Security features for the present invention include a unique worldwide address identification number for accessing the device prescriptions, and loss or theft identification with a global positioning system beacon to locate the device anywhere in the world and activate or deactivate the controller if required. One embodiment of the present invention includes an authentication means that verifies the patient's and/or doctor's fingerprints before the apparatus can be initiated. When using the Internet, the environmental control unit can be programmed and analyzed by downloading statistical data back to the doctor providing patient progress. In one embodiment, the environmental control unit can receive system updates and repairs that are performed on-line from a personal computer by means of an input/output device, such as a RS-232 port. Further, the electronic control device may offer a liquid crystal display with a soft glow backlight showing features such as a multi-segment battery status, mode of dispensing indicator, temperature display in Fahrenheit/Centigrade, vibration treatment timer with stealth vibrator indicator, dosage cycle counter, electronic safety and sleep indicator, treatment locked menu selection with real status indicators, processing power for multiple modes of dispensing, preset pulsating and automatic run dispensing features. This controlled supervision and independence allows the patient and doctor to determine and/or prescribe the rate, frequency, and timing of aerosol prescriptions while the patient enjoys the opportunity to live a more normal life.

In another aspect of the present invention, an operating system is provided with the present nebulizer device, which includes device firmware code and a software program for managing the doctor's prescription for treatment. The communication of the doctor's prescription to the patient is accomplished by a software program arrangement using a personal computer port connection in conjunction with a phone call from a landline or a cell phone signal. The medicine-nebulizing device is powered in one embodiment with a standardized battery operation providing virtually a muted operation so the patient realizes a relaxed environment for treatment. This device is more efficient, effective and comfortable than conventional nebulizer systems for asthma patients. In another embodiment of the present invention the nebulizer operates under free physical pressure. More specifically, the nebulizer is equipped with a venturi or inductor device which increases the velocity of the incoming gas thereby creating a localized low pressure area which facilitates agent mixture and inhalation.

It is a further aspect of the present invention to utilize a portable refillable compressed gas, such as highly concentrated oxygen ($O_2$), as opposed to an electrical motor to generate compressed gas. The use of portable compressed gas such as oxygen serves two purposes. The first is to introduce a cooler, higher density gas into the patient's lungs, which may allow the breathing passages to realize a deeper penetration and absorption of the required medication for treatment. The deeper penetration into the lungs may allow for a quicker physiological response resulting in a faster event recovery as well as less medication requirements suggesting the treatment to be a more efficient process than conventional methods. In one embodiment of the present invention the compressed gas is 95% oxygen with the remaining 5% of gas consisting of Nitrogen ($N^2$), Argon (Ar) or other compatible gas similar to the requirements of an oxygen concentrator. This process may also reduce the duration time and the amount of medication required for each treatment, thus making it a very efficient and effective system. Although, compressed oxygen is the preferred method of gas delivery to the patient, one skilled in the art will appreciate that many other compressed gases such as purified air, Nitrogen ($N_2$), and Argon (Ar) may be employed. Secondly, the compressed gas would provide sufficient energy to pressurize the entire nebulizer system and dispense the required medication to the patient between about 35 and 70 degrees Fahrenheit and which further acts as a cooling mechanism for a pump motor and/or control valve as it passes through each controlling component in the device. Thus, in one embodiment of the present invention, a disposable gas cartridge administrator is provided to support and contain a pressurized gas cartridge and to regulate the flow of compressed gas to the internal passages of the pressure regulator.

It is thus a further aspect of the present invention to provide an improved gas regulator with reduced size and convenient geometric configuration for portable and convenience use. This requirement is needed to accommodate special constraints in many other medical apparatus. It is another aspect of the present invention to provide an improved gas regulator, which provides a high degree of resistance to sustained pressure within the regulator body. It is also a particular aspect of the present invention to provide an improved gas regulator, which includes a flow control mechanism for selectively controlling the pressure and rate of gas, as well as purity of the gas, which travels through the regulator body.

It is another aspect of the present invention to provide a medicine chamber that is capable of receiving one or a plurality of medicinal agents. Depending on the patient's condition, treatment with different agents at different times may be required. The medicine chamber may be equipped with the means to dispense the desired medication from a plurality of medications without mixing the agents. In another embodiment of the present invention the agent is compressed into thin strips or wafers that are inserted into a plurality of slots in the medicine chamber. Alternatively, a patient may need a plurality of agents administered concurrently which is achievable by the same dispensing means.

As may be appreciated by one skilled in the art, it is another aspect of the present invention that this device may also be utilized in other areas of alternative medicinal treatments such as homeopathic, herbal, mineral, and vitamin health, wherein different types of medicines and drugs can be quickly and effectively administered to a patient in the form of a cooled gas, such as high oxygen concentration gas.

Thus it is one aspect of the present invention to provide a method for monitoring and administering an atomized liquid medication from a portable, compressed gas cartridge, that comprises the steps of:

providing a cartridge administer adapted for receiving a portable cartridge of a high pressure gas;

reducing the pressure of the high pressure gas to a reduced pressure gas having a pressure no greater than about 50 psig;

generating a plurality of aerosol sized particles from said reduced pressure gas which have a diameter no greater than about 3 microns;

introducing a predetermined dose of a prescribed medicine into a stream of said aerosol sized particles to create a prescribed medicinal gas; and dispensing said prescribed medicinal gas to a patient at a predetermined rate of flow through an oral dispensing apparatus.

DETAILED DESCRIPTION

Figure 1:
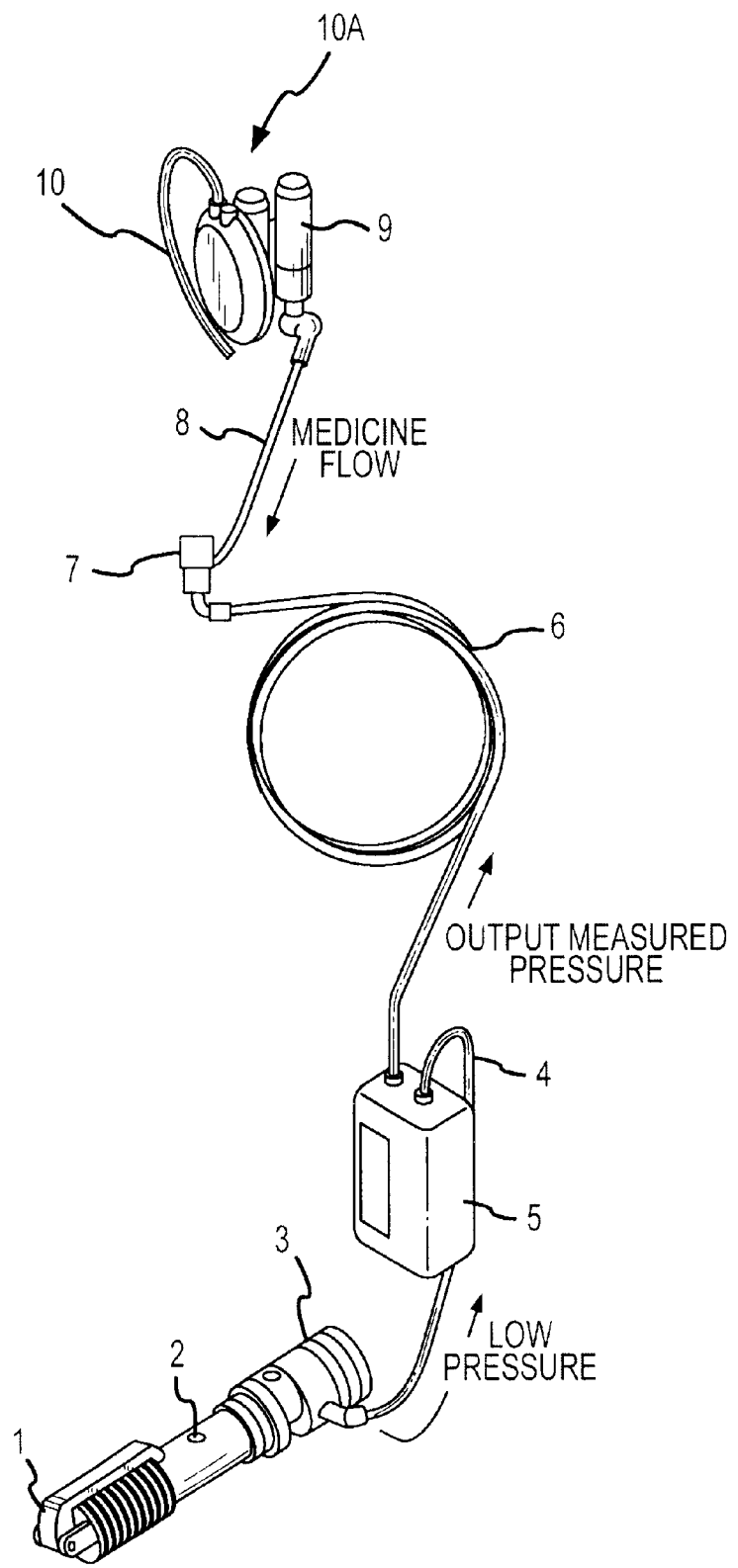
FIG. 1 is a perspective view of a medicinal nebulizer system, including a cartridge administrator, environmental control unit, nebulizer and headset dispenser.
Figure 2:
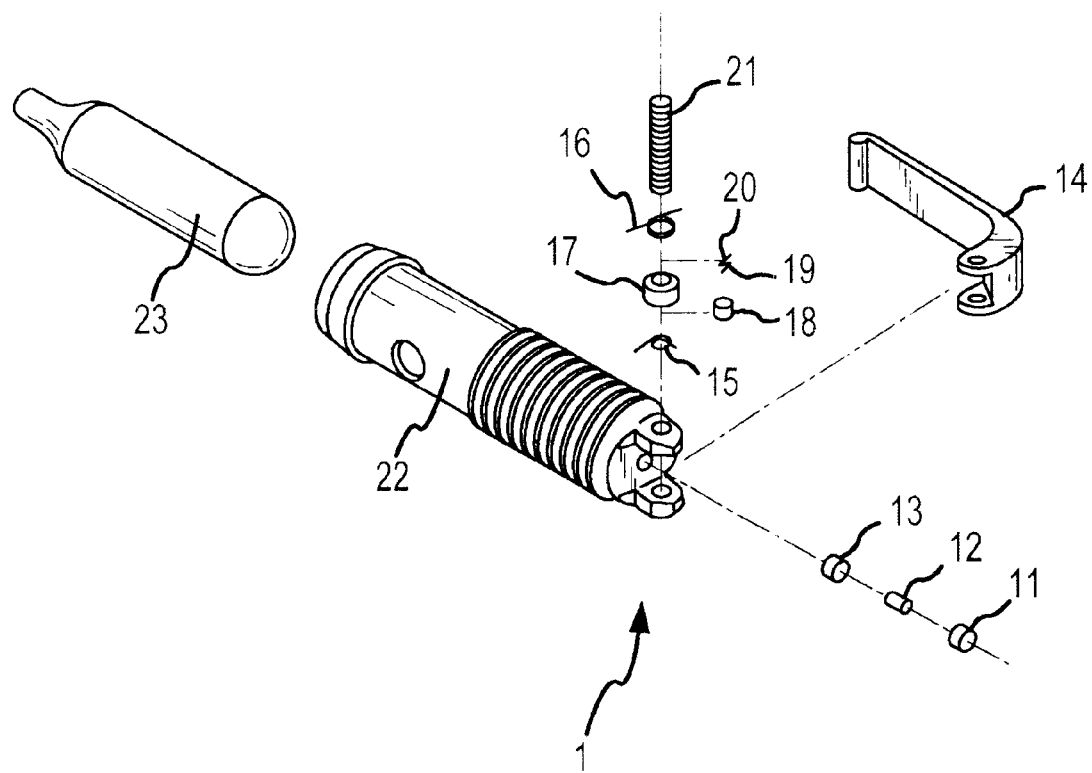
FIG. 2 is a exploded perspective view of the cartridge administrator and associated gas cartridge.
Figure 2A:
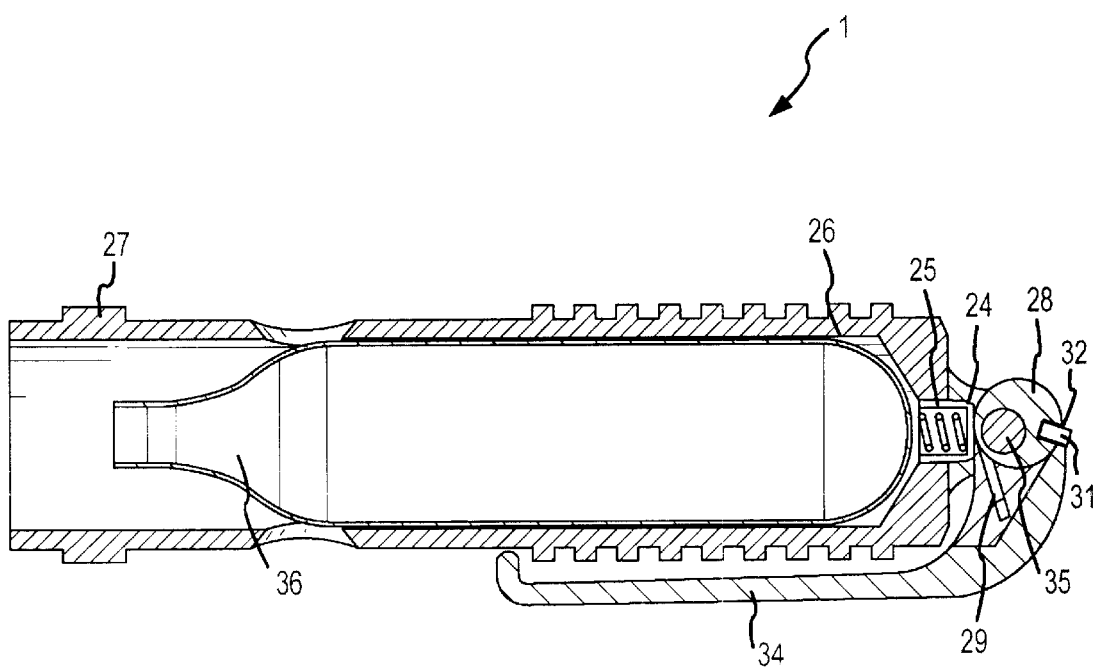
FIG. 2A is a cross-sectional view of the cartridge administrator shown in FIG. 2 with associated gas cartridge.
Figure 2B:
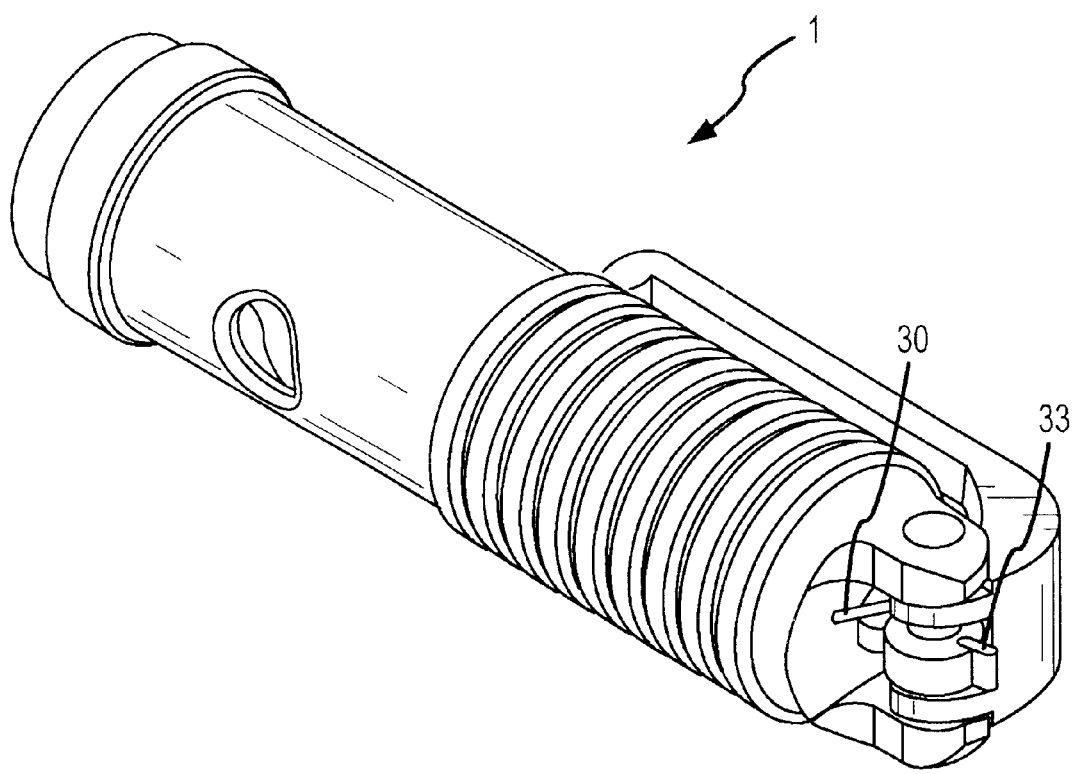
FIG. 2B is a perspective view of the cartridge administrator of FIG. 2A.

Referring now to FIGS. 1–8 a medicinal nebulizer system, components thereof, and a method of use are shown herein. In one embodiment of the present invention, a patient uses a medicine module that delivers medicine to a nebulizer mouthpiece and an audio pad that delivers instructions or entertainment during treatment. The nebulizer mouthpiece is additionally connected to an environmental control unit via a tube. A user-activated source of high-pressure delivery gas is reduced in pressure by a pressure regulating system and delivered to the environmental control unit via a second tube to further regulate the flow, which ultimately regulates the dose of medicine the patient will receive. Finally, after exiting the environmental control unit the regulated and monitored gas flow is fed into the nebulizer mouthpiece where it combines with the medicine to form an atomized mist that is inhaled by the patient.

Unit Assembly and System Operation

Referring now to FIG. 1, a unit assembly of one embodiment of the present invention which generally consists of ten major component sub-assemblies is shown herein. The sub-assemblies include a cartridge administrator 1; a high pressure gas cartridge 2; a pressure regulator 3; a length of tubing 4 interconnecting an environmental control unit to the pressure regulator; an environmental control unit 5; another length of tubing 6 interconnecting the nebulizer and mouthpiece to the environmental control unit; a nebulizer and associated mouthpiece 7; a medicine delivery tube 8; a medicine chamber delivery system 9 which is utilized to administer the drugs and other medicines to the patient; and an earpiece 10 with audio comfort pad. In general, the cartridge administrator 1 holds the high pressure gas cartridge 2 and is interconnected in operable communication with the pressure regulator 3, which reduces the pressure of the compressed gas from as much as about 2,500 psi to between about 10 psi and 20 psi. Once the high pressure $O^2$ gas cartridge is positioned in the pressure-reducing regulator and released, a 6 liter to 18 liter supply of $O^2$ gas at a pressure of between 10–20 psi is discharged from the gas pressure regulator into a tube, which transports the low-pressure gas to the environmental control unit 5. As mentioned briefly above, a preferred embodiment of the present invention utilizes pressurized oxygen as a carrier gas, however, one skilled in the art will appreciate that any number of gasses may be used such as, purified air, Nitrogen ($N_2$), and Argon (Ar). Furthermore, the present invention is not to be construed to be limited to be used strictly with pressurized oxygen.

The pressure of the $O^2$ gas has now been reduced to between about 10 and 25 psi as it exits the pressure regulator 3 through a short piece, i.e., 6.0 inches of 2 millimeter polyethylene tubing to the environmental control unit 5. The environmental control unit 5 senses the incoming $O^2$ gas and associated pressure, and through a control valve suppresses for a count of time in milliseconds a measurement of gas to be dispensed, and further filters the oxygen gas through a 99.9% HEPA filter to remove any impurities. The oxygen gas then flows to the nebulizer and associated mouthpiece 7 positioned in operable communication with a headset dispenser 10A through a longer piece of polyethylene tubing 8 by means of patient breath activation or control panel management on the environmental control unit device 5. The nebulizer 7 is designed to disrupt the incoming flow of fluid from the headset dispenser 10A and vaporize the fluid into micron size particles for inhalation by mixing the medicinal fluid and oxygen flowing downstream from the environmental control unit 5. In one embodiment, the nebulizer 7 is comprised of polypropylene plastic and/or stainless steel mechanical components.

The headset dispenser 10A is operably positioned and interconnected to the nebulizer and mouthpiece 7 and is generally worn by the patient over the ear like a common set of earphones for electronic type devices. The headset device 10A also supplies the handheld medicinal nebulizer 7 assembly with the required prescribed medications by means of a disposable medicine chamber 9 attached to the headset dispenser 10A.

In brief summary, the medicinal nebulizer system of the present invention utilizes a high pressure oxygen contained in a disposable or refillable portable high pressure cartridge 2, reduces and filters the oxygen (to remove any impurities) to a usable pressure of approximately 8 psi to 25 psi, measures the refined gas product through a digital electronic controller that discharges precise amounts of oxygen gas, and directs the oxygen gas into the nebulizer, which forms a fusion with the medication fluid that is supplied and dispensed by means of a headset device 10A worn by the patient. For greater clarity, each of the individual components is discussed in greater detail herein below.

Cartridge Administrator

To support a high pressure, disposable compressed $O^2$ gas cartridge 23 requires a cartridge administrator 1 as seen in FIG. 2. This device utilizes a lever cam mechanism at the base of the body 22 of the cartridge administrator for positioning and discharging between about 8 and 25 grams of oxygen generally at a rate of between about 6 and 18 liters per minute from a disposable-compressed $O^2$ gas cartridge 23. A shock base 11, compression spring 12, and a plunger 13 are fitted to a center bore in the base of the device. The lever 14 assembly is generally provided with a small torsion spring 15, a large torsion spring 16, lever cam 17, an "over-travel" limiting mechanism 18, a left locating pin 19, and a right locating pin 20 which are fitted to the two legs of the base of the body 22 of the cartridge administrator with a force fit roll pin 21 to hold the components in place to the body 22.

The large opening of the cartridge administrator 1 is faced and laminated in one embodiment with a color sleeve representing the universal color code for a given delivery gas, such as green for oxygen. An between about 8 and 25-gram disposable compressed $O^2$ gas cartridge 23 is placed into the cartridge administrator 1 with the narrow neck of the disposable compressed $O^2$ gas cartridge 23 facing outward toward the large opening of the cartridge administrator 1. The completed unit is hand threaded to a snug fit onto a male/female base of the high-pressure regulator. In this position the disposable compressed $O^2$ gas cartridge 23 inside the cartridge administrator 1 is ready to be discharged as necessary by depressing a lever 14 at the base at any time to release the compressed $O^2$ gas into the high-pressure regulator device.

FIG. 2 is an exploded isometric view of a first exemplary embodiment of the cartridge administrator 1 constructed in accordance with the present invention. FIG. 2 illustrates one embodiment of a compressed $O^2$ gas regulator device which is adapted for use with an aerosol inhalation apparatus suitable for treating and/or prophylaxis of pneumonia and other disorders involving medications, and which can be dispensed in aerosol form. To provide additional detail, FIG. 2a is a collapsed axially cut cross-sectional view of the device shown in FIG. 2, and which illustrates the various components of the compressed $O^2$ gas cartridge administrator 1. FIG. 2b is a perspective end view of the device shown in FIG. 2, and which depicts the positioning of the compressed $O^2$ gas container 36 within the administrator and which illustrates various components on the opposite side of the lever assembly of the compressed $O^2$ cartridge administrator 1 and which is suitable for use in the aerosol inhalation apparatus.

The device shown in FIG. 2a includes a shock base 24 which is used to seat a compression spring 25 inside a plunger 26 through a bore in the base 22 of the compressed $O^2$ gas cartridge administrator 1. Using the lever cam 28 as the lever assembly starting point, a large torsion spring 29 is situated on one side of the lever cam 28. A small torsion spring 30 (FIG. 2b) is placed onto the opposite side of the lever cam 28. An over travel limiter 31 is fitted into a slot in the lever cam 28. An over travel limiting pin left 32 (FIG. 2a) is positioned into the lever cam 28 via a pair of apertures in the lever cam 28 to the over travel limiter 31. The over travel limiting pin right 33 (FIG. 2b) is also positioned into the lever cam 28 via a pair of apertures in the lever cam 28 to the over travel limiter 31. The cam mechanism assembly and the lever 34 are fitted to the base of the cartridge administrator 1 by means of a roll pin 35.

A disposable compressed $O^2$ gas cartridge 36 is placed into the compressed $O^2$ gas cartridge administrator 1 and seated onto the plunger 26. The compressed $O^2$ cartridge administrator 1 is used in conjunction with the operation of a high-pressure gas regulator device discussed below. When required, and on demand, the lever 34 is manipulated by the patient to activate the lever cam mechanism 28, thus pushing the plunger 26 upward toward the regulator device piercing mechanism and thus releasing the compressed $O^2$ gas from the disposable, high pressure compressed $O^2$ gas cartridge 36.

Gas Pressure Regulator

Figure 3:
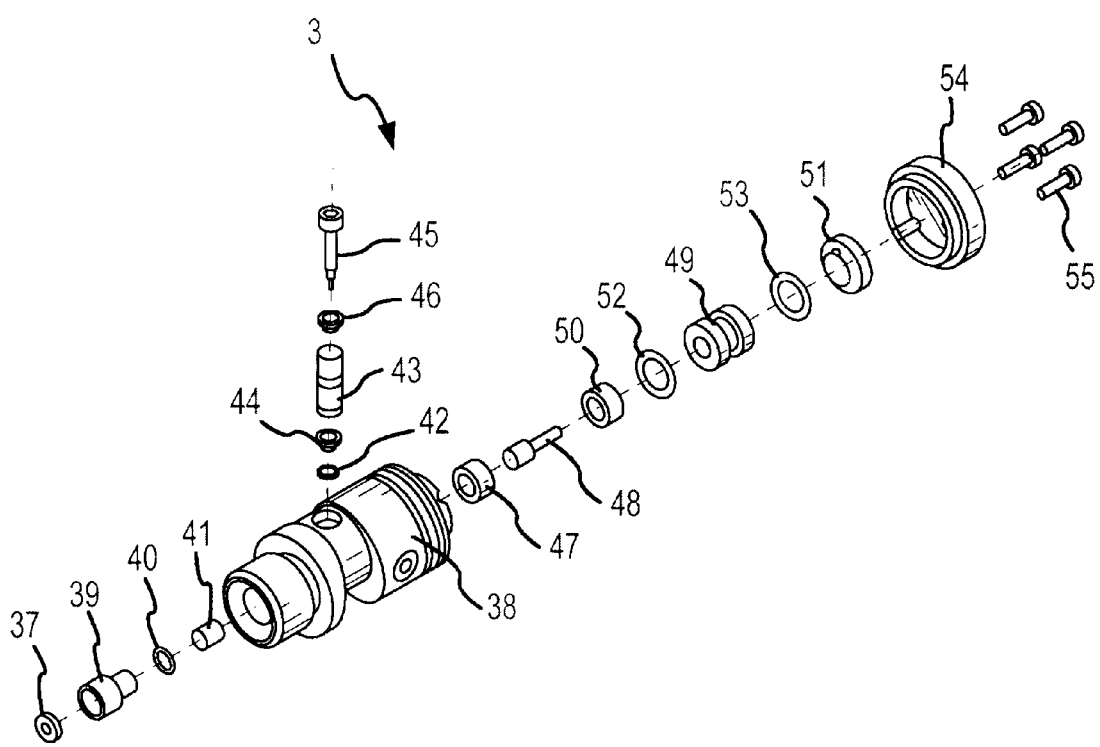
FIG. 3 is an exploded perspective view of the gas regulator associated with FIG. 2A.
Figure 4:
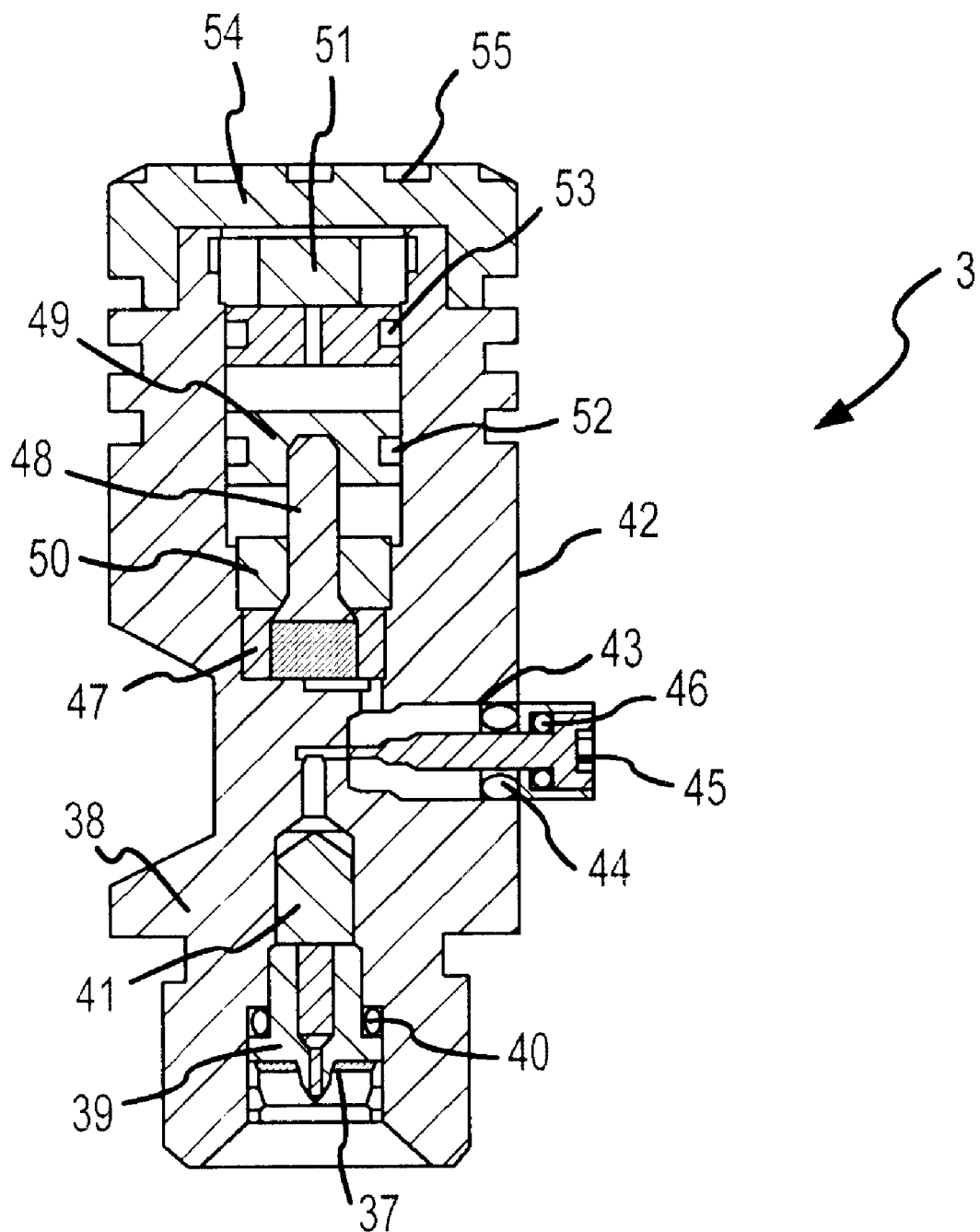
FIG. 4 is a cross-sectional view of the gas regulator shown in FIG. 3.
Figure 4A:
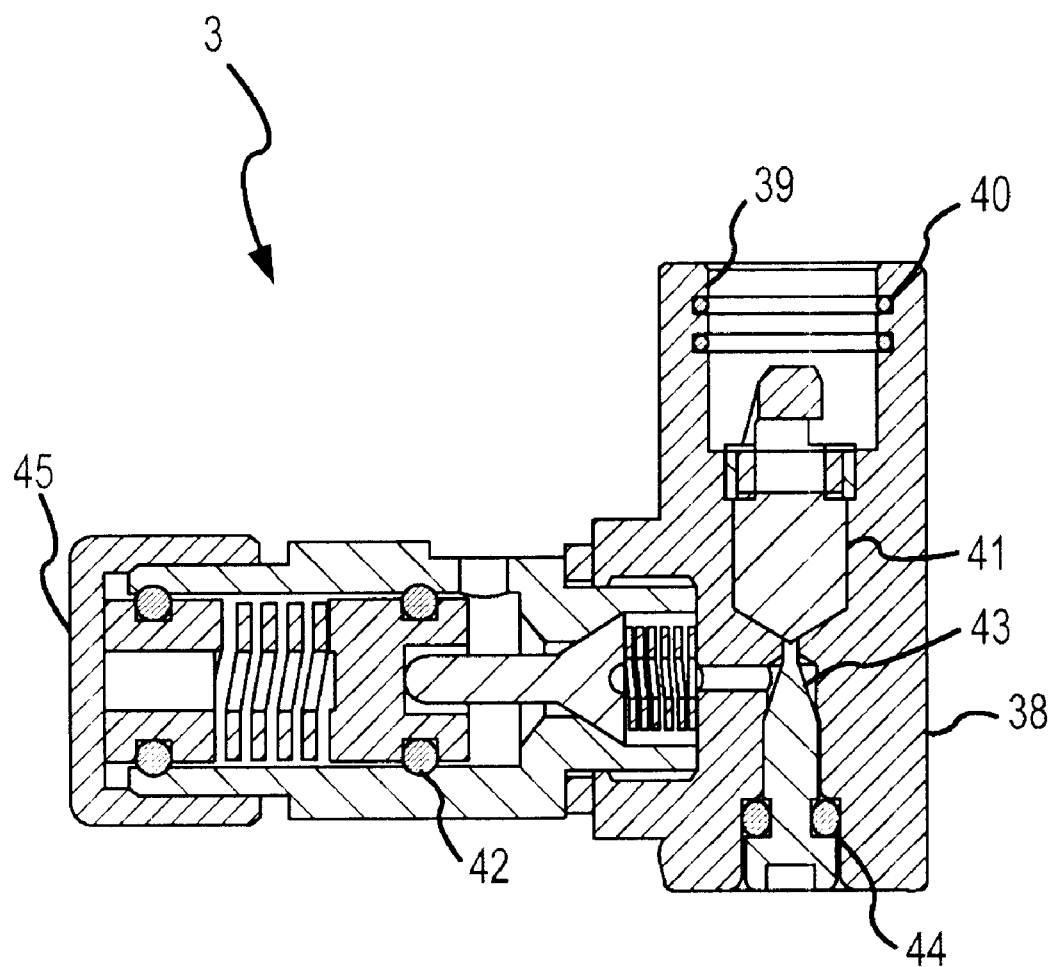
FIG. 4A is a cross-sectional view of an alternate embodiment of a gas regulator.
Figure 4B:
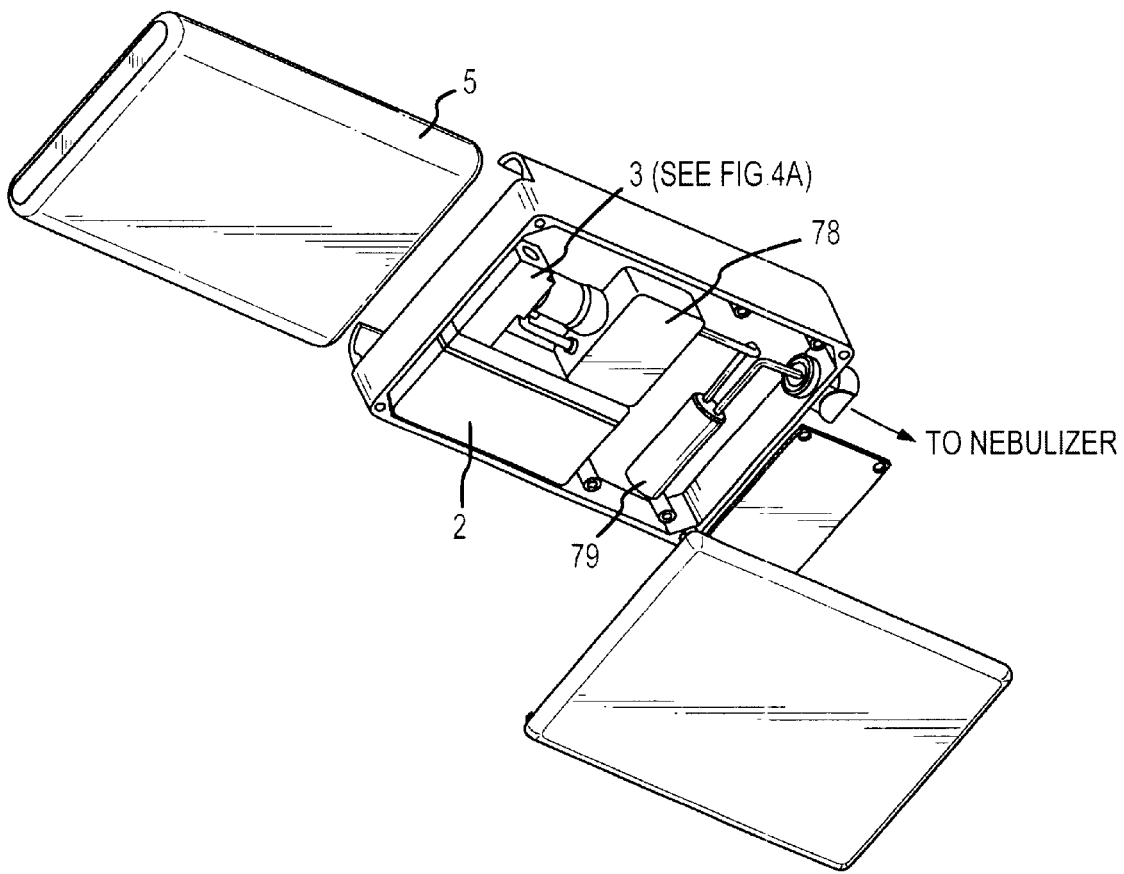
FIG. 4B is a perspective view of a combination gas cartridge, gas regulator, and environmental control unit.

Referring now to FIG. 3, an exploded isometric view of a first exemplary embodiment of the compressed gas regulator 3 device for an aerosol inhalation apparatus suitable for treating and/or prophylaxis of pneumonia and other disorders involving medications, which can be dispensed in aerosol form is shown herein. A self-contained gas pressure-reducing regulator is provided herein as one of the novel concepts of the present invention and which generally comprises a body member having a pressure induction system, a flow control system, a pressure transfer mechanism, and an outlet conduit control system used to produce properly sized gas particles. The pressure-reducing regulator 3 thus is used in conjunction with a high-pressure $O^2$ gas cartridge to take high-pressure oxygen gas from between about 500 and 2500 psi and reduce the pressure to between about 10 and 25 psi for available use for inhalation purposes.

The pressure-reducing gas regulator apparatus 3 requires a source of compressed air to be communicated to the pressure induction system of the body member 38, which is supplied from the cartridge administrator as described above. The compressed air immediately flows through a main filtration mechanism positioned into the primary bore of the pressure induction system, which is used to remove any impurities and to further reduce pressure.

The volume of compressed $O^2$ gas that flows to the high-pressure regulator 3 preferably is in the range of between about 6 and 18 liters at atmospheric pressure. The gas pressure is then reduced to approximately 10 psi to 25 psi (0.69 BAR–1.72 BAR). The flow rate of compressed air, which flows to the patient, is preferably between about 1 and 5 liters per minute and can be interrupted as necessary based on the breathing pattern of the patient. Excess oxygen gas may be vented as necessary. It is thus anticipated that one disposable high pressure or gas cartridge will be used for each given treatment; although it is feasible that one cartridge may be used for multiple treatments depending on the dosage, severity of asthma attack, etc.

The portable pressure regulator 3 includes in one embodiment a disposable molded filter 41 which is produced from a porous media substrate and which is designed to impede the rate of flow of oxygen, but further to retain the generated ice crystals which develop as a result of a pressure drop. The filtration media also restricts other potential contamination and impure particles from entering into the regulator flow control system. The disposable filter 41 may also be calibrated to any micron particle size depending upon the application requirements of the pressure regulator device. However, in general the porous media has a size of about 100 microns, and more preferably about 40 microns, and a length of between about 0.10 and 1.0 inches.

A flow control system is integral to the pressure regulator body 38 and is designed to effectively reduce the velocity and pressure of the high-pressure oxygen gas entering the pressure regulator device. The flow control system is used to limit the rate and pressure at which gas flows to the pressure transfer mechanism. A calibrated adjustment device positioned prior to the pressure transfer assembly is used to selectively adjust the rate at which the pressurized gas enters into the outlet conduit control assembly via a transfer port from the flow control assembly. In general, the flow control system works by biasing the adjustment screw clockwise to reduce the velocity and counter-clockwise to increase the velocity at which the high-pressure oxygen gas bleeds along the shaft of the adjustment screw 45 until it reaches the exit port into the gas pressure transfer chamber.

The gas pressure transfer chamber interconnects the passageway from the flow control system to the outlet conduit control system. The gas pressure transfer chamber in one embodiment contains a helix stem 48 mounted for limited movement in an axial direction between an upper position closing the gas transfer outlet, and a lower position opening the gas transfer outlet so as to permit controlled gas to flow between control systems. Alternatively, other types of biasing means may be utilized for the same purpose. Further, a closure cap is mounted to the body member 38 to define a pressure control chamber on the outlet passage side of the helix stem 48, the closure cap 50 biasing the helix piston 49 to provide venting of the upper chamber region to the atmosphere.

The outlet conduit control system consists of a calibrated helix piston 49, which is biased to control the opening and closing of the gas transfer chamber of the regulator 3 and thus the flow rate of the compressed gas. A drawing identifying one embodiment of the helix stem 48 spring may be seen in FIG. 7, and which identifies a helix spring 48 manufactured by Helical Products Co., Inc. A calibrated adjustment cap 51 atop the regulator assembly 3 is used to monitor and control the volume of flow exiting the regulator body 38 via a side exhaust port, and may be adjusted to within 10 pounds per square inch by simply rotating the adjustment cap in a clockwise or counter clockwise rotation to decrease or increase the rate of flow, respectively.

Referring now to FIG. 4, a cross-sectional view of the device shown in FIG. 3, and which illustrates the gas pressure-reducing regulator 3 that is suitable for use in the aerosol inhalation apparatus is shown herein. A washer 37 is used to seat a disposable compressed gas cartridge used in conjunction with the operation of the regulator device. The compressed gas then flows into the regulator body 38 through a threaded gas insert member 39. An O-ring 40 is used to seal the compressed gas from venting past the threaded gas insert member 39 and the regulator body 38. In one embodiment of the present invention, a commercially available O-ring sold under the Model No. PRP568-009 by PARCO, Inc. may be used.

Compressed oxygen gas continues to flow from a conduit centered in the threaded gas insert member 39 and into an internal bore containing a 40-micron particle filter 41. The 40-micron filter 41 limits the amount of debris and/or ice build-up from the compressed gas which potentially could enter the regulator device. The compressed gas then flows through from the bore to an L-shaped conduit intersection of the regulator body 38 and continues forward to an O-ring 42 and the flow control housing 43. In one embodiment of the device, a commercially available O-ring sold under the Model No. PRP568-003 by PARCO, Inc. is used.

The O-ring 42 is used to seal the compressed gas from venting past the flow control housing 43 and the regulator body 38. An O-ring 44 is used to seal residual compressed gas that may vent past the threads on the flow control housing 43. In one embodiment of the device, a commercially available O-ring sold under the Model No. PRP568-006 by PARCO, Inc. was used.

To adjust the flow rate of compressed gas, the calibrated adjustment screw 45 is turned counter clockwise to open the passageway for the compressed gas to enter the flow control housing 43 at a flow rate corresponding to the amount of turns of the calibrated adjustment screw. An O-ring 46 is used to seal the compressed gas from venting past the calibrated adjustment screw 45 internally. Turning the calibrated adjustment 45 clockwise will close the passageway stopping the compressed gas from entering into the flow control housing 43. Turning the calibrated adjustment screw 45 counterclockwise opens the passageway for the compressed gas to enter the flow control housing 43 and exit through a second L-shaped conduit leading to the pressure control assembly.

Compressed gas then enters the center transfer chamber of the support bushing 47 forcing the helix piston stem 48 upward into the helix piston 49. The piston stem 48 is captivated by means of a lower pressure plate 50 threaded into the regulator body 38. The lower pressure plate 50 limits the travel of the helix piston stem 48 pushing into the piston 49. Compressed gas then enters the chamber between the lower pressure plate 50 and the helix piston 49 forcing the helix piston 49 upward through the upper pressure plate 51. A bottom O-ring 52 is used to seal the lower end compressed gas and the top O-ring 53 is used to prevent venting past the top of the helix piston 49. In one embodiment of the present invention, a commercially available O-ring sold under the Model No. PRP568-012 by PARCO, Inc. of 2150 Parco Avenue, Ontario, Calif. 91761 was used.

An upper pressure plate 51 is used to captivate the helix piston 49. The upper pressure plate 51 in one embodiment has two lateral spanner holes for adjusting the rate of flow. Turning the upper pressure plate 51 counter clockwise decreases the rate of compressed gas exiting and flowing downstream to the environmental control unit, by allowing the piston stem 48 to gradually seal against the under side of the lower pressure plate 50. The upper pressure plate 51 allows for travel of the helix piston 49 and the helix piston stem 48 to completely seal the passageway of compressed gas from the center transfer chamber of the support bushing 47. Turning the upper pressure plate 51 clockwise increases the compressed gas volume exiting to atmosphere through the side exhaust port by forcing the helix piston stem 48 to gradually release the pressure seal against the under side of the lower pressure plate 50. Manipulating the upper pressure plate 51 clockwise or counter clockwise determines the desired rate of pounds per square inch of regulated pressure. A pressure regulator cap 54 sits atop the regulator device captivated to the regulator body 38 by four machine screws 55.

As opposed to other prior art pressure regulator devices such as those commonly found in applications such as scuba driving devices, the present invention provides a novel, lightweight device capable of taking a high-pressure gas from between about 500 and 2,500 psi to an operable working pressure of between about 10 and 25 psi in a span of approximately 1.0–5.0 inches. One novel aspect of this device may generally be attributed to the combination of the gas filter 41, adjustment screw 45 and the magnetic physics of the lower pressure plate 50 that uniquely retains the exclusive calibrated helix piston stem 48 as it biases the exclusive calibrated helix spool 49 achieving extremely high precision for gas pressure and volume control over a wide spectrum of pressures and flow rates.

Referring now to FIG. 4B, a sub-assembly for use in one embodiment of the present invention is shown herein. The sub-assembly embodies at least the gas cartridge 2, the gas regulator 3, and the environmental control unit 5. The gas cartridge 2 is selectively interconnected to the sub-assembly, and in one embodiment rechargeable. When the gas cartridge is detached, pressurized gas may be fed directly into the gas regulator 3, for example during clinical use. During normal use the gas cartridge feeds high-pressure gas through a valve to the gas regulator 3. The substantially lower pressure gas is then fed into a second holding chamber 78 which releases a predetermined amount of gas with the actuation of a valve 79. This valve 79, which is controlled by the environmental control unit 5, may actuate to release a predetermined amount of gas that is tailored to the patient's breathing pattern or as needed to provide the most efficient agent delivery to the patient. The environmental control unit 5 is also selectivity integrated to the sub-assembly. To monitor collected data or to alter an embedded program, the environmental control unit 5 is simply removed and put in communication with another computer. Alternatively, the environmental control unit 5 may be adapted to receive wireless communications.

Environmental Control Unit

Referring now to FIG. 5, a front elevation view of one embodiment of an environmental control unit 5 that is used in conjunction with the handheld medicinal nebulizer apparatus of the present invention is shown herein. A cross-section of the environmental control unit 5 used in conjunction with the present invention may be seen in FIG. 5. More specifically, the environmental control device includes a printed circuit board assembly with liquid crystal display monitor with push button controls, piezo valve with optimum gas flow dynamics, breath and voice actuated dose requirement sensor, video micro camera for doctor/patient interface, rechargeable 6 volt lithium ion battery with enhanced charging cycle, and a disposable 5-micron filter. A compressed gas regulator device and a disposable compressed gas cartridge-holding device are used in conjunction with the electronic controller device to produce properly sized particles as a mist. In a preferred embodiment, the compressed gas regulator device and the disposable compressed gas cartridge with holding mechanism reside internal to the environmental control unit as an integral part of the headset itself and not as an independent subassembly as shown in FIG. 1.

In operation, compressed oxygen gas is supplied to the piezo valve attached to the electronic controller device through a conduit from the compressed gas regulator device that is preset to approximately 10 psi–25 psi of pressure. A signal from either the breath or voice activated sensor required by the patient or a manual push button attached to the electronic controller device releases the gas from the piezo valve through a conduit to an in-line disposable 5-micron filter, through the extending conduit to the Nebulizer device attached to the patient headset device. The flow of compressed oxygen gas is provided to the patient at a rate of between about 1 and 5 liters/min and can be interrupted based upon personal or prescribed settings.

Figure 5:
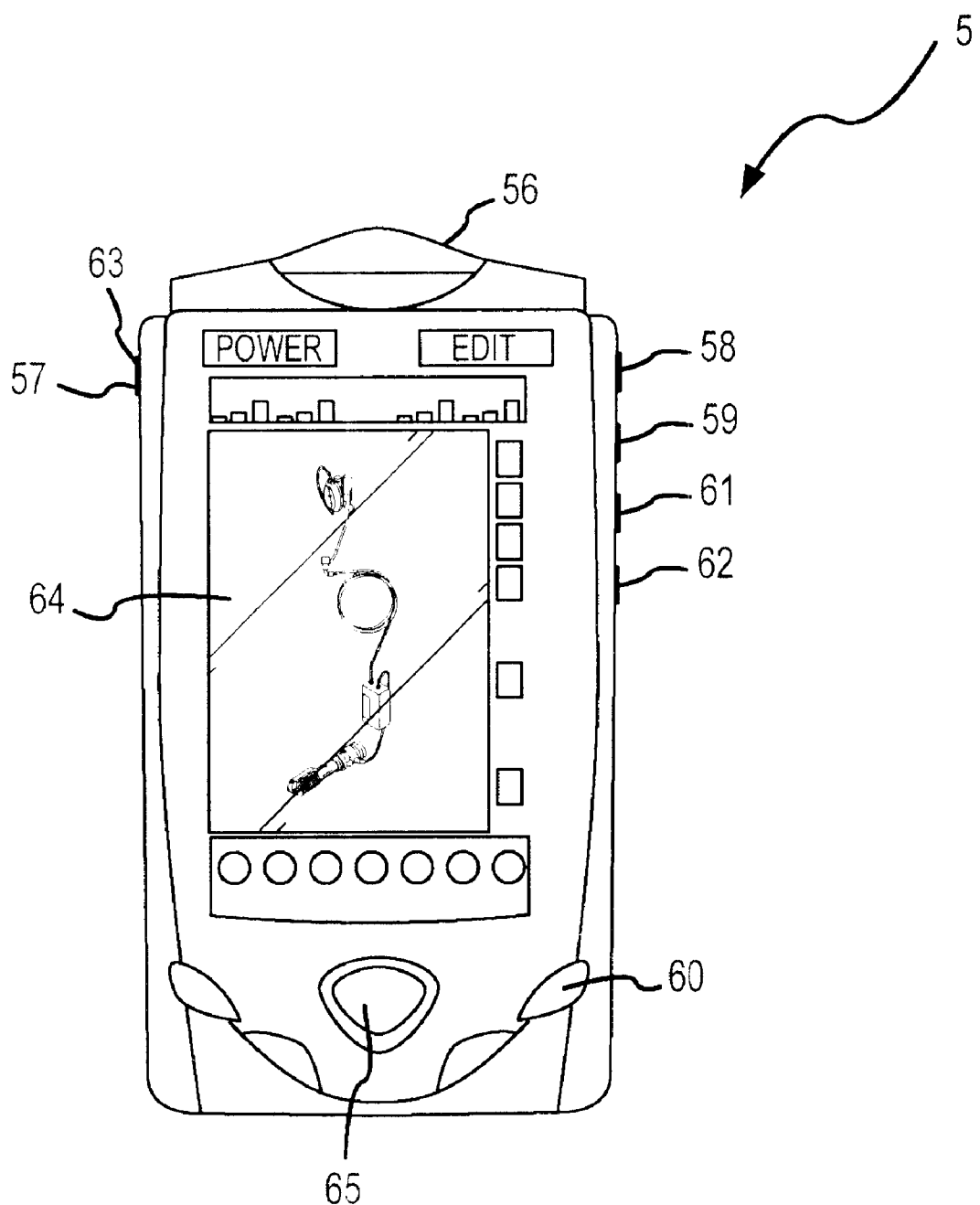
FIG. 5 is a front elevation view of the environmental control unit shown in FIG. 1.

FIG. 5 further identifies the controller used in conjunction with the present invention. It consists in one embodiment of a micro video camera 56. The power inlet 57 is a port used to charge the nebulizer device by means of a conventional 120 VAC outlet. The mode features in one embodiment twenty-six modes of dispensing that may be selected. The dispensing modes are programmed in the nebulizer including five modes that the patients may program themselves by using the data link control. A control button 58 is used for preset dispensing modes such as normal breath activation, or alternatively an automatic predetermined cycle count such as activating once every four seconds.

The control button 59 is used to determine the rate of dispense (ROD) feature and records the highest rates of dispense that are actually achieved over a 1-second period. This data is constantly updated should the new reading exceed the previous reading. The patient or attending physician can zero the rate of dispense feature at any time. The control button 60 has a panic mode for full emergency use, and has a maximum rate of dispense limit (MROD) feature. Certain dispensing modes have governing limits and are not adjustable. The rate of dispense can not be set greater than what the patient's nebulizer is capable of delivering. The control button 61 is used for flow control adjustments, which is predetermined and properly calibrated using specific equipment. In one embodiment, the maximum flow rate provided is about 18 liters/min. Electronic dwell is what determines the control valve opening and closing time. A longer dwell uses more gas than a shorter dwell. Adjustment is only recommended if the patient wishes to fine-tune the headset dispenser to specific accessories. In one embodiment, an optimum 'setting is 14 milliseconds, with adjustments ranging from 10 milliseconds to 24 milliseconds. The control button 62 in one embodiment is designed to control the treatment timer, alarm, battery status, device temperature, and PIN control features.

In a preferred embodiment, the environmental control unit will be an integral part of the headset itself and not an independent subassembly as shown in FIG. 1. The environmental control unit mechanism will be fully automated and reside internal to the earpiece worn by the patient. Power requirements to drive the microprocessor are a lithium ion battery and will last about 5 years before replacement. The micro valve coordinating the medication flow as signaled from the environmental control unit mechanism is a state of the art membrane substrate that only requires about a micro-volt to activate and operate program requirements. An addition to the headset, a visual flip screen may be provided to send and receive information for all aspects of the calibration and functionality of the device.

The "vibration" timer is an interactive treatment timer that alerts the patient when a scheduled treatment is due to start or is completed. This program helps to lessen the stress during a normal treatment session. The timer can be set in one-minute increments from the first dose, which allows the patient to focus on the treatment interaction. The timer will activate and reset every minute and the last ten seconds at the end of the treatment program. The battery status is indicated at all times by a four-segment display. Power is drawn while the nebulizer has power connected. To prevent power discharge the Tab Key 63 is locked at the end of treatment. The Tab Key 63 utilizes the same port as the power inlet 57. The last segment indicates the number of doses remaining with an atomizer being powered. If the patient has entered a PIN number, this feature allows you to lock or unlock the nebulizer. The PIN feature will help to prevent unauthorized use. The LED display 64 is backlit and shows all operations of the device. The 2-way trigger 65 is used to dispense only when this button is activated.

Nebulizer and Headset Dispenser

Figure 6:
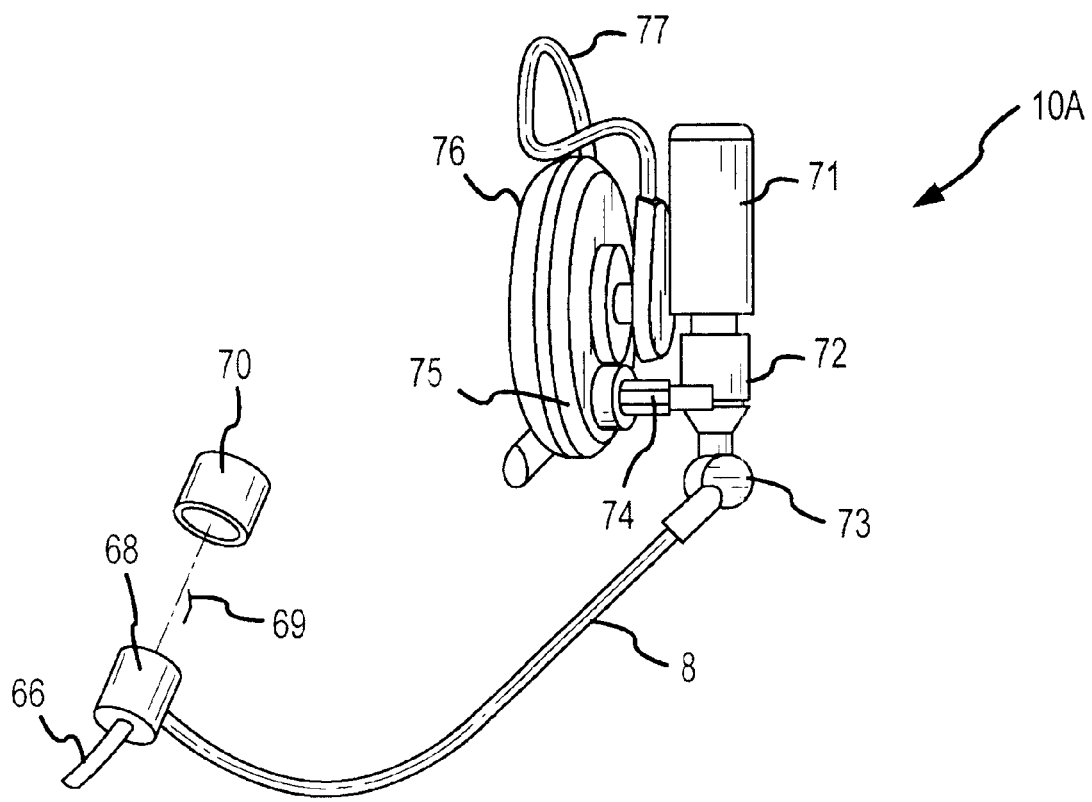
FIG. 6 is a perspective view of the headset dispenser and nebulizer shown in FIG. 1.
Figure 7A:
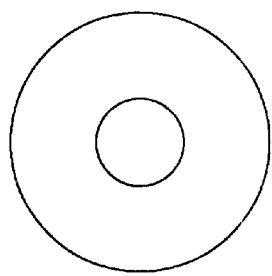
FIG. 7 is a front elevation and end views of a helical machined spring used as a biasing device in the cartridge administrator and associated pressure regulator.
Figure 7B:
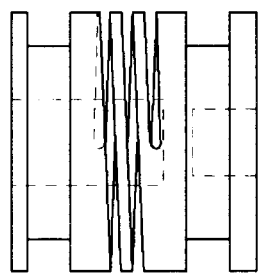
Figure 7C:
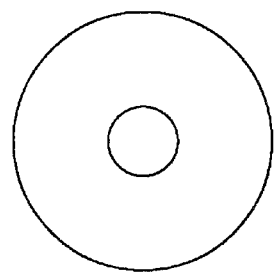

Referring now to FIG. 6, an isometric view of a first exemplary embodiment Portable Handheld Nebulizer and associated headset is provided which in one embodiment is approximately the size of a miniature cellular phone and weighs approximately 1 pound and utilizes a rechargeable, quick connect battery to operate. It is portable enough to allow some critical patients to leave home periodically to travel and not require the use of an electrical outlet. The medicine chamber is disposable, unique, and completely integrated into the patient's state-of-the-art headset providing hands-free operation. The headset also houses the prescription medication modules and may utilize in one embodiment a media player adaptor, compact disc adaptor, video micro camera or other similar device for patient relaxation during normal treatments. The media player mechanisms will also support patient training of the device as well as communication from the doctor via the Internet.

More specifically, the nebulizer works by first receiving a low gas pressure at a predetermined flow rate from the environmental control system 5. As shown in FIG. 1 the medication flow is gravity fed and drawn out like a vacuum by the air pressure in the mouthpiece as it is received from the environmental control system 5. As shown in FIG. 6, the oxygen gas supply 66 from the environmental control system 5 and the medication supply 67 intersect at the mouthpiece 68 and atomize at the nozzle 69 which is disseminated through the shroud 70 for inhalation by the patient. In a preferred embodiment, the microprocessor will coordinate and send a dosage of medication to the mouthpiece and at the same precise time send a dosage of oxygen gas pressure to the mouthpiece. The atomization function using this method becomes much more accurate and efficient for patient inhalation achieving greater results.

FIG. 6 further illustrates a headset dispenser device that is generally suitable for use as an aerosol inhalation apparatus, and which generally comprises a nebulizing shroud 70 that provides communication of the atomized medication to the patient. Preferably, the geometry of the nozzle 69 internal to the nebulizer and the shape of the nebulizer shroud 70 create a pattern effect with the discharged particles. The pattern may be selected to be in the form of a fan, circle, diamond, linear, or a combination of geometrical shapes. The patterns demonstrate where the dose concentration is dispensed allowing for variances in patient head geometry.

The aerosol nozzle 69 is preferably a modified stainless steel tube with unique porting used to discharge medication and gas to the patient for inhalation. The aerosol nozzle 69 is ultrasonically welded into the dispensing cup 68. The dispensing cup 68 holds the aerosol nozzle 69 and the nebulizing shroud 70 collectively as a unit. The nebulizing shroud 70 is interchangeable with different size nebulizing shrouds allowing for alternative atomizing patterns. The dispensing cup 68 may be specially bonded or ultrasonically welded to the fluid supply tube 67 and the gas supply tube 66 for collecting and dispensing the medication and gas to the patient. The fluid supply tube 67 supplies the flow of medication from the medication module 71 passing through the medication module holder 72 and the directional supply arm 73. The medication supply assembly is attached to the headset connector 74 and the earpiece support 75. The cushioned earpiece 76 may be fitted to the patient by means of a quick connect ear loop mechanism 77 which is interchangeable for additional types and sizes and which provides the patient further versatility and comfort. The gas supply tube 66 supplies the flow of oxygen gas from the environmental control unit 5 and the gas pressure regulator 3 assemblies to the headset dispenser assembly to allow for commingling of the oxygen gas and the prescribed medicine which is delivered from the medication module.

Method of Use

Figure 8:
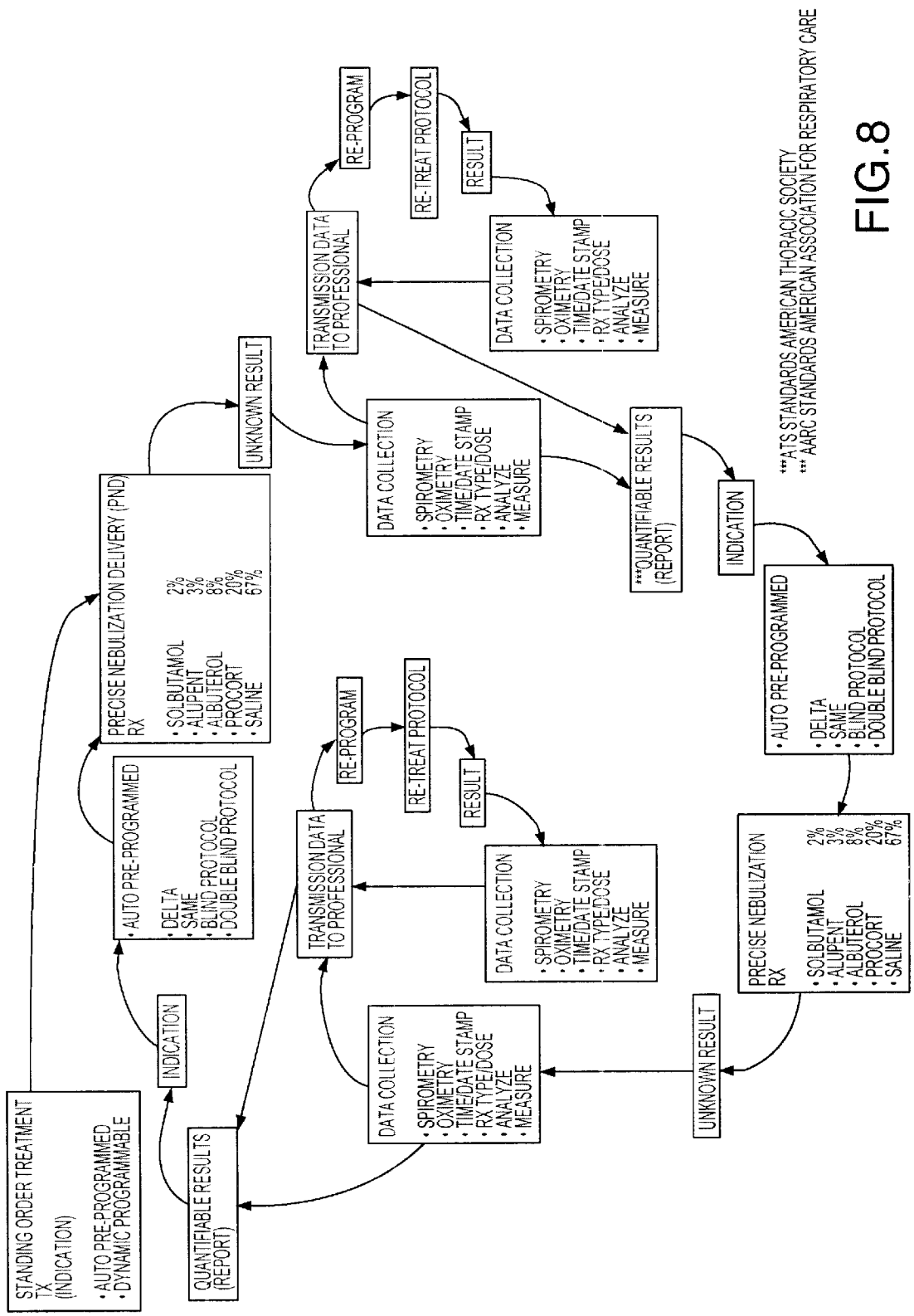
FIG. 8 is a flow diagram of one method of using the medicinal nebulizer system shown in FIG. 1.

Referring now to FIG. 8, an example of a method of using the present invention is shown herein. Initially, a standing order treatment is prescribed by the doctor that sets a precise nebulization delivery to the patient. Upon activation or the system the originally prescribed dosage is administered. Next, as the patient exhales, predetermined data is collected and transmitted to a doctor for in-person review or a computer with a preprogrammed doctor protocol. This output data is analyzed in light of the set protocol either by the doctor personally or by the preprogrammed software. Depending on the outcome of the comparison, a new dosage may then be transmitted back to the patient for manual dosage alteration or, preferably, directly to the disbursal device for automatic adjustments. In an alternative embodiment of the present invention the doctor-selected protocol is downloaded or otherwise communicated to the environmental control unit which is capable of initiating agent delivery, monitoring the delivery, and altering the delivery based on the protocol.

For clarity purposes the following numbering and components associated therein are included below:

| # | Component |
|---|---|
| 1 | Cartridge administrator |
| 2 | High pressure gas cartridge |
| 3 | Pressure regulator |
| 4 | Poly tubing (6") |
| 5 | Environmental control unit |
| 6 | Poly tubing (36.0") |
| 7 | Nebulizer and mouthpiece |
| 8 | Medicine delivery tube |
| 9 | Medicine chamber/delivery system |
| 10 | Audio comfort pad |
| 10A | Headset device |
| 11 | Shock base |
| 12 | Compression spring |
| 13 | Plunger |
| 14 | Lever |
| 15 | Torsion spring, small |
| 16 | Torsion spring, large |
| 17 | Lever cam |
| 18 | Over-travel limiter |
| 19 | Locating pin left |
| 20 | Locating pin right |
| 21 | Roll pin |

-continued

| # | Component |
|---|---|
| 22 | Administrator body |
| 23 | Oxygen gas cartridge |
| 24 | Shock base |
| 25 | Compression spring |
| 26 | Plunger |
| 27 | Cartridge administrator body |
| 28 | Lever cam |
| 29 | Torsion spring, large |
| 30 | Torsion spring, small |
| 31 | Over-travel limiter |
| 32 | Locating pin left |
| 33 | Locating pin right |
| 34 | Lever |
| 35 | Roll pin |
| 36 | Oxygen gas cartridge |
| 37 | Delrin washer |
| 38 | Regulator body |
| 39 | Threaded gas insert member |
| 40 | O-ring |
| 41 | Filter 40 micron porous media |
| 42 | O-ring |
| 43 | Flow control housing |
| 44 | O-ring |
| 45 | Adjustment means |
| 46 | O-ring |
| 47 | Support bushing |
| 48 | Helix piston stem |
| 49 | Helix piston spool |
| 50 | Lower pressure plate |
| 51 | Upper pressure plate |
| 52 | O-ring bottom |
| 53 | O-ring top |
| 54 | Pressure regulator cap |
| 55 | Machine screws |
| 56 | PCBA, environmental control unit |
| 57 | Power inlet |
| 58 | Control button, preset dispensing |
| 59 | Control button, rate of dispense |
| 60 | Control button, panic |
| 61 | Control button, flow control |
| 62 | Control button, accessories |
| 63 | Tab key |
| 64 | LED display |
| 65 | 2-way trigger |
| 66 | Oxygen gas supply tube |
| 68 | Mouthpiece dispenser cup |
| 69 | Nozzle |
| 70 | Shroud |
| 71 | Medication module |
| 72 | Module holder |
| 73 | Directional supply arm |
| 74 | Headset connector |
| 75 | Ear piece support |
| 76 | Comfort audio pad |
| 77 | Ear loop connector |
| 78 | Gas chamber |
| 79 | Valve |

The foregoing description of the present invention has been presented for purposes of illustration and description. Furthermore, the description is not intended to limit the invention to the form disclosed herein. Consequently, variations and modifications commenced here with the above teachings and the skill or knowledge of the relevant art are within the scope in the present invention. The embodiments described herein above are further extended to explain best modes known for practicing the invention and to enable others skilled in the art to utilize the invention in such, or other, embodiments or various modifications required by the particular applications or uses of present invention. It is intended that the dependent claims be construed to include all possible embodiments to the extent permitted by the prior art.

What is claimed is:

1. A method for monitoring and administering an atomized liquid medication from a portable, compressed gas cartridge, comprising the steps of:

providing a cartridge administer adapted for receiving a portable cartridge of a high pressure gas;

providing a first medicine chamber, which is adapted to receive at least a first medicine;

providing a second medicine chamber, which is adapted to receive at least a second medicine;

providing a medicine delivery system that is adapted to selectively disperse at least one of said first medicine, said second medicine, and a mixture of said first medicine and said second medicines, to create a predetermined dose of prescribed medicine;

reducing the pressure of the high pressure gas to a reduced pressure gas having a pressure no greater than about 50 psig;

generating a plurality of aerosol sized particles from said reduced pressure gas which have a diameter no greater than about 3 microns;

introducing said predetermined dose of prescribed medicine from said medicine delivery system into a stream of said aerosol sized particles to create a prescribed medicinal gas; and dispensing said prescribed medicinal gas to a patient at a predetermined rate of flow, wherein said prescribed medicinal gas is adapted to treat a medical condition.

2. The method of claim 1, wherein said high pressure gas is substantially oxygen.

3. The method of claim 1, further comprising the steps of filtering said high-pressure gas.

4. The method of claim 1, further comprising the step of modifying said dispensing step from a remote location.

5. The method of claim 1, further comprising the step of storing historical data related to said dispensing step.

6. The method of claim 1, further comprising the step of modifying a concentration of said prescribed medicine from a remote location.

7. The method of claim 1, wherein the combination of said cartridge administrator and said portable cartridge of a high pressure gas weigh less than about 0.50 pounds.

8. The method of claim 1, further comprising the step of providing a source of music or instructions to a patient receiving said prescribed medicinal gas.

9. The method of claim 1, further comprising the step of providing a global positioning system which is interconnected to an apparatus utilized in said dispensing step to locate said apparatus if said apparatus is lost or stolen.

10. The method of claim 1, wherein said reduced pressure gas has a temperature of between about 35 and 70 degrees Fahrenheit.

11. The method of claim 1, wherein said reducing the pressure of the high-pressure gas step utilizes a gas pressure regulator with a length no greater than about 3.0 inches.

12. The method of claim 1, wherein said high-pressure gas has a pressure of at least about 1000 psi.

13. A method for monitoring and administering an atomized liquid medication from a portable, compressed gas cartridge, comprising the steps of:

providing a cartridge administer adapted for receiving a portable cartridge of a high pressure gas;

providing a disposable first medicine chamber, which is adapted to receive at least a first medicine;

providing a disposable second medicine chamber, which is adapted to receive at least a second medicine;

providing a medicine delivery system that is adapted to selectively disperse at least one of said first medicine, said second medicine, and a mixture of said first medicine and said second medicine, to create a predetermined dose of prescribed medicine;

receiving a patient-supplied security input to ensure said predetermined dose of prescribed medicine is being dispensed to the proper patient;

reducing the pressure of the high pressure gas to a reduced pressure gas having a pressure no greater than about 50 psig;

generating a plurality of aerosol sized particles from said reduced pressure gas which have a diameter no greater than about 3 microns;

introducing said predetermined dose of prescribed medicine into a stream of said aerosol sized particles to create a prescribed medicinal gas;

providing a headset dispensing device with a plurality of dispensing modes including at least one of a preset pulsating mode and an automatic run dispensing mode;

dispensing said prescribed medicinal gas to a patient at a predetermined rate of flow if said patient-supplied security input is properly authorized by one of a doctor, a nurse, a medical school student, a medical resident, a holder of a power of attorney, a parent, a guardian, a technician, and a computer;

monitoring the patient's response to said dispensation of said medicine; comparing said patient's response to a protocol approved by a medical professional; and modifying, if necessary, said predetermined dose of prescribed medicine or said predetermined rate of flow to conform with said protocol, wherein said monitoring is substantially continuous to ensure the most effective treatment for the patient.

14. The method of claim 13, wherein said monitoring is performed remotely by a medical professional.

15. The method of claim 13, wherein said monitoring and said comparison step is performed remotely by a computer program.

16. The method of claim 13, wherein said monitoring is performed by a unit operably interconnected to said cartridge administer which is pre-programmed with said protocol prior to a patient's use.

17. A method for monitoring and administering an atomized liquid medication from a portable, compressed gas cartridge, comprising the steps of:

providing an environmental control unit adapted to perform predetermined functions which include at least one of a regulating dosage of medicine, a regulation of air pressure, a monitoring of medicine intake, and a monitoring of a patient's response to treatment;

providing a cartridge administer adapted for receiving a portable cartridge of a high pressure gas;

receiving inputs that indicate a patient's condition;

comparing said inputs with a predetermined protocol;

analyzing said comparison to determine a preferred amount of a medicine dosage required;

analyzing a patient-supplied security input to ensure said medicine dosage is being dispensed to the proper individual;

reducing the pressure of said high pressure gas to a reduced pressure gas;

generating a plurality of aerosol sized particles from said reduced pressure gas;

introducing said medicine dosage into a stream of said aerosol sized particles to create a prescribed medicinal gas;

providing a headset dispensing device adapted for positioning at least partially on the patient's head; and dispensing said prescribed medicinal gas through said headset dispenser to a patient at a predetermined rate of flow.

* * * * *